United States Patent [19]

Garza Flores et al.

[11] Patent Number: 5,360,616

[45] Date of Patent: Nov. 1, 1994

[54] INJECTABLE PHARMACEUTICAL COMPOSITION

[75] Inventors: Josue Garza Flores; Laura P. Laiseca Soto, both of Mexico City, Mexico; Jose Guillen Pichardo, Sto Domingo, Dominican Rep.; Juan Angeles Uribe, Mexico City, Mexico

[73] Assignee: Applicaciones Farmaceuticas S.A. De C.V., Mexico City, Mexico

[21] Appl. No.: 714,583

[22] Filed: Jun. 13, 1991

[30] Foreign Application Priority Data

Jun. 14, 1990 [FR] France ................. 90 07416

[51] Int. Cl.[5] ................. A61K 9/14; A61K 31/56
[52] U.S. Cl. ................. 424/489; 514/169; 514/178; 264/5; 264/13
[58] Field of Search ................. 424/489, 499–502; 514/169, 178; 264/5, 13

[56] References Cited

U.S. PATENT DOCUMENTS

| | | | |
|---|---|---|---|
| 3,773,919 | 11/1973 | Boswell et al. | 424/19 |
| 3,928,566 | 12/1975 | Briggs | 424/94 |
| 4,147,767 | 4/1979 | Yopel | 424/489 |
| 4,244,949 | 1/1981 | Gupta | 424/943 |
| 4,349,530 | 9/1982 | Royer | 424/19 |
| 4,349,580 | 9/1982 | Royer | 424/19 |
| 4,384,975 | 5/1983 | Fong | 427/213.36 |
| 4,745,907 | 5/1988 | Russel, Jr. et al. | 128/1.1 |
| 4,748,024 | 5/1988 | Leonard | 424/489 |
| 4,837,381 | 6/1989 | Steber et al. | 424/502 |
| 4,892,734 | 1/1990 | Leonard | 424/422 |
| 4,963,367 | 10/1990 | Ecanow | 424/485 |
| 5,019,400 | 5/1991 | Gombotz et al. | 424/497 |

FOREIGN PATENT DOCUMENTS

| | | |
|---|---|---|
| 0210875 | 4/1987 | European Pat. Off. . |
| 0257368 | 8/1987 | European Pat. Off. . |
| 1116795 | 6/1968 | United Kingdom . |
| WO88/07816 | 10/1988 | WIPO . |
| 90/13285 | 11/1990 | WIPO . |

OTHER PUBLICATIONS

J. Garza Flores, et al., "Assessment of a New Low--Dose Once–A–Month Injectable Contraceptive," *Contraception*, vol. 35, No. 5, May (1988).

"Encyclopedia of Chemical Technology, Third Edition," vol. 15, John Wiley and Sons, pp. 470–493 (1981).

Institut national de la Propriete Industrielle, "Rapport de Recherche," (Search Report), Feb. 12, (1991).

*Primary Examiner*—G. S. Kishore
*Attorney, Agent, or Firm*—Mason, Fenwick & Lawrence

[57] ABSTRACT

Formulations of programmed-release medicinal products intended for parenteral administration by injection, comprising calibrated solid microspheres (1 to 300 microns) of active substances. Provided in this form, steroids (for example progesterone and 17-$\beta$-estradiol) may constitute injectable contraceptives, and the action of drugs having an approximatively 24 hours lasting effect may be regulated and extended.

5 Claims, 14 Drawing Sheets

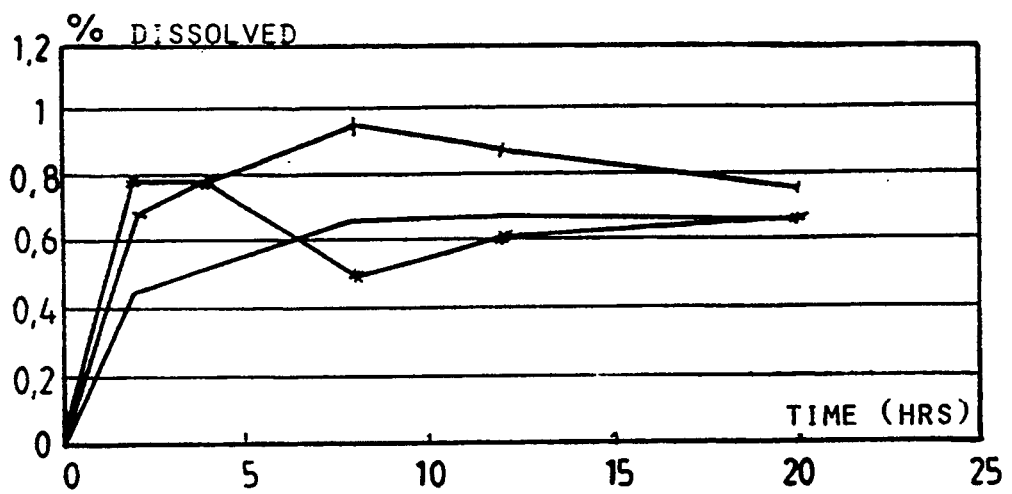
FIG. 10 — DISSOLUTION PROFILE NAPROXEN, MICROSPHERES
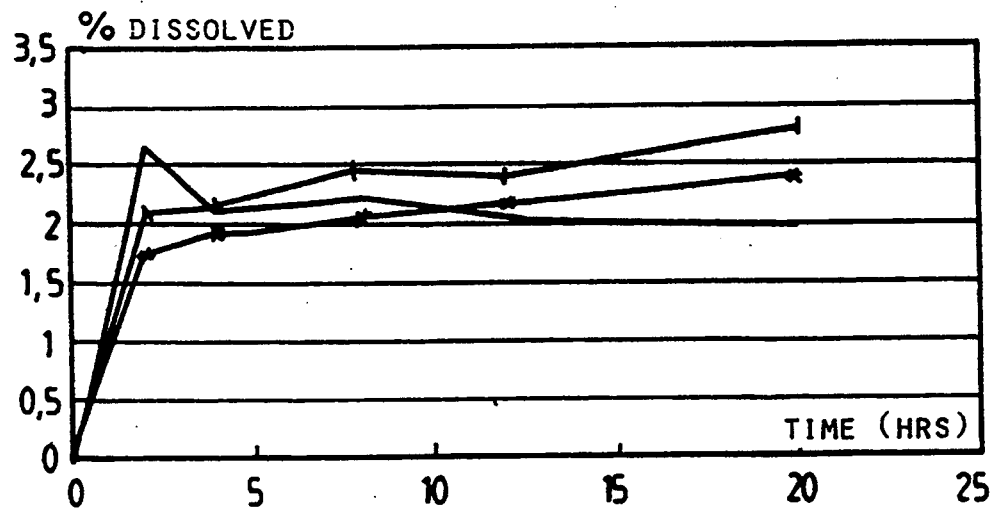
FIG. 11 — DISSOLUTION PROFILE NAPROXEN, CRYSTALS

FIG. 14
PROGESTERONE PLASMA LEVELS IN RABBITS AFTER INJECTION OF 150 MG. OILY SOLUTION
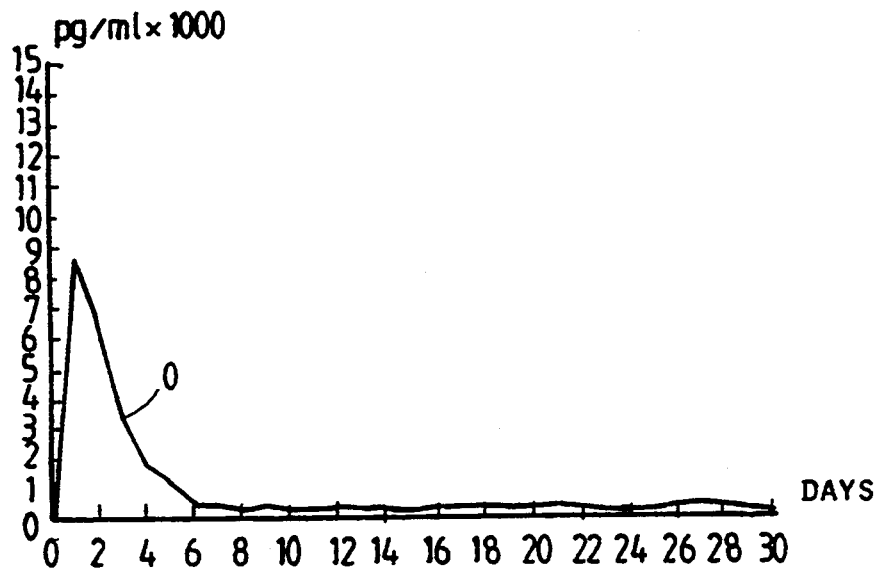
PROGESTERONE PLASMA LEVELS IN RABBITS AFTER INJECTION OF 150 MG. CRYSTALS (44 μM), AQUEOUS SUSPENSION (2 ML)
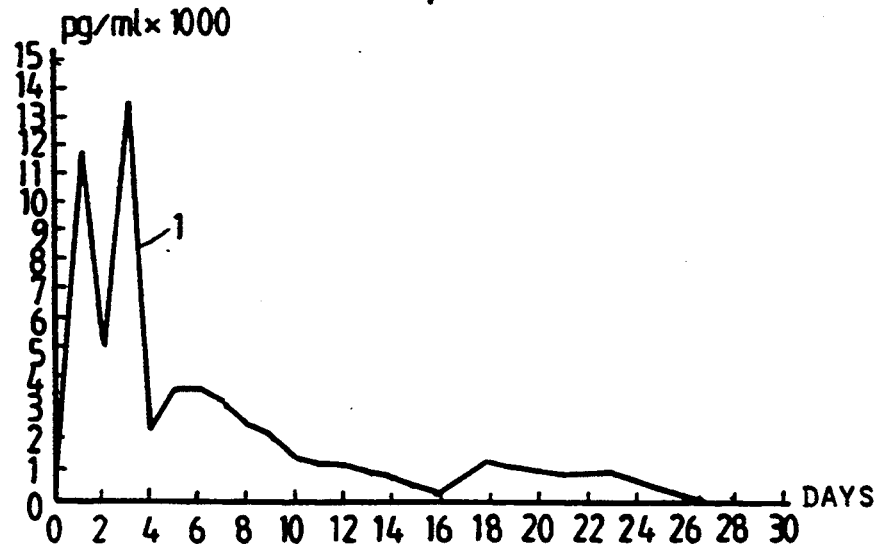
FIG. 15

PROGESTERONE PLASMA LEVELS IN RABBITS AFTER INJECTION OF 150 MG MICROSPHERES (44 μM), AQUEOUS SUSPENSION (2 ML)

ESTRADIOL PLASMA LEVELS IN RABBITS AFTER INJECTION OF 5 MG, OILY SOLUTION

DISSOLUTION PROFILE INDOMETHACIN, CRYSTALS

DISSOLUTION PROFILE INDOMETHACIN, MICROSPHERES

INJECTABLE PHARMACEUTICAL COMPOSITION

FIELD OF THE INVENTION

The present invention relates to a process for improving the control of the pharmacokinetic and pharmacological properties of pharmaceutically active substances. It relates also to particles of active substances, and their use in delayed-release injectable formulations.

PRIOR ART

Biologically active substances, weakly soluble in a physiological medium, have already been used in the form of a suspension of particles and administered by intramuscular injection in order to obtain a slow dissolution and therefore a prolonged effect in the human or animal organism. For example, mixtures of norethisterone and mestranol, in the form of crystalline powder in aqueous suspension of have been tested for the manufacture of an intramuscular injectable contraceptive (J. Garza Flores et al., Contraception, May 1988, Vol. 35, No. 5, 471–481).

Probably because of particle size variations and particle shape irregularities, these prior art compositions generally exhibit several defects:

Curve for the release of active substances exhibiting a sharp peak just after the injection and then a descending slope, which increases the total dose necessary to obtain an adequate, lasting effect.

Occasional formation of lumps or crusts in the suspension.

Necessity to use large diameter hypodermic needles in order to avoid the risk of a blockage in the syringe outlet.

The patent FR 2 070 153 (DUPONT DE NEMOURS) describes suspensions of particles of active ingredients coated with polylactide polymer matrices. This technique decreases the initial medicament shock effect and slows the release of the active substance. However, the shape irregularities create, in this case as well, a risk of operative incident at the time of injection, and the variations in shape, size and internal composition of these particles cause an undesirable variability in the rates of dissolution in the receiving organism, that is to say a dispersion of results which does not permit a precise pharmacokinetic prediction.

The patent EP No. 257 368 (AMERICAN CYANAMID CO) describes a composition for parenteral use consisting of microspheres of fats and/or waxes, of natural or synthetic origin, of low melting point (40°-60° C.), loaded with particles of a polypeptide, for example a growth hormone. When these compositions are injected into cattle, the dissolution of the growth hormone is delayed by the wax or fat coating, which prolongs its presence in the animal organism, causing an increase in growth or in lactation. These microspheres have a tendency to deform, to agglutinate or to coalesce when the ambient temperature is high, particularly in tropical countries (40°-60° C.), which may cause handling or storage problems. As the proportion of active polypeptide in the particle is limited in practice to 30-40%, the injection of these particles also has the disadvantage of introducing into the organism a quantity of carrier substance which is foreign and useless to this organism, and which is at least of the order of 1.5-3 times that of the active substance.

Several coating or microencapsulation techniques have been used in the prior art, part of which is described for example in "Encyclopedia of Chemical Technology, " 3rd edition, volume 15, pages 470 to 493 (1981), JOHN WILEY AND SONS. The microcapsules thus formed often contain "central" particles of very different size, or no central particle at all. The prior art microspheres or microcapsules permit a slow dissolution and therefore an overall delayed release of the active ingredients. However, given the shape and mass heterogeneities of the central particles or of dispersed ultra-fine particles which may be coated in capsules of similar external dimension, the rate of release of the active ingredient is not homogeneous and a fine control of the release, or a finely programmed release as a function of time is not possible.

Furthermore, from a pharmacological point of view, the reproducibility and the reliability of the results obtained with these prior art preparations are not adequate for certain applications, for example contraception, which constitutes an obstacle to their practical use on a large scale.

Such a programmed release is desirable nevertheless, in particular when the action of the biologically active substance has to coincide with a natural biological cycle of the human or animal organism (for example menstrual) or when it is important (for example in the case of an analgesic, an alkaloid, a cardiotonic and the like) that the rates of release are well controlled in order to avoid any period of overdose or on the contrary of underdosage at the time of an injection subsequent to an earlier injection.

SUMMARY OF THE INVENTION

The aim of the present invention is to provide delayed-release formulations for administration by parenteral injection, intended for example for the applications mentioned in the preceding paragraph, which allow a fine control of this release without exhibiting the disadvantages of particle suspensions or of microcapsules of the prior art.

This aim is achieved by virtue of the use of solid, non-porous and calibrated microspheres consisting substantially of pharmaceutically active substances.

The rate of dissolution of a microsphere in a given solvent medium (preferred target medium: the internal physiological medium) is essentially a function of the radius of the sphere, taking into consideration the relationships between volume, area and radius of a sphere.

According to one aspect of the present invention, the use of solid, non-porous spheres makes it possible to have a precise knowledge of the mass-surface relationship of particles and therefore, by virtue of a selection of the size of the spheres, that is to say of the radius or of a distribution of radii, to have a precise control of the rate of release of the active ingredient or active ingredients administered. This control precision, by avoiding overdosages or the need to compensate for underdosages, makes it possible to reduce the total administration of the biologically active substance or active substances to the minimum quantity required in order to obtain the desired therapeutic effect and thereby decrease the risk of producing undesirable secondary effects in the patient.

Used in the form of pure active ingredients, the microspheres according to the present invention have the advantage, compared to the coated or microencapsulated particles of the prior art, of decreasing the volume of solid material which has to be injected into a living organism. They further have the advantage of not using a low-melting excipient (m.p. <60° C.), those particles could agglutinate and cause handling problems upon injection.

They also have the advantage of not introducing unnecessary solid excipient, more or less degradable, into the organism.

Some substances may be combined with adjuvants not directly active on the receiving organism: the combination may comprise various pharmaceutically acceptable additive means for increasing the stability or chemical integrity of the biologically active substances, it being understood that they are not vector type excipients. In particular, it may become useful to decrease the melting point or to inhibit a decomposition reaction during the microsphere manufacturing process (for example by melting-freezing).

Relative to suspensions of pure active ingredients in the form of particles of irregular shapes known in the prior art, the microspheres according to the present invention have the advantage of a lesser tendency to agglutinate and of passing in a more fluid manner through a hypodermic needle. Moreover, microspheres may be classified and separated more finely and more reliably as a function of their size than irregularly shaped particles.

The formulation according to the present invention may be provided in the form of microsphere powder in vials-ampoules ready for making into a suspension, or in the form of a suspension ready prepared in injectable ampoules ready for administering in human or veterinary medicine. The suspension medium may be water, a saline solution, an oil containing the buffers, surfactants or preservatives conventionally employed in injectable suspensions by pharmaco-technicians, or any other substance or combination which does not threaten the physical and chemical integrity of the substances in suspension and which is suitable for the organism which will receive it. If it is desired to avoid a sudden initial elevation of the level of active ingredient in the internal medium of the receiving organism, the use will be preferred, in the case of ready-for-use suspensions, of liquid vectors in which the said active ingredients are practically insoluble. In the case of active substances partially soluble in the lukewarm liquid vector but insoluble at cold temperature, it is preferable, from the pharmacological point of view, to avoid the formation of precipitates (called "caking" effect) by preparing formulations in the form of separate microsphere powder and liquid vector which will be mixed only at the time of injection.

In veterinary applications where the duration of desired effect may be very long (for example lactation period of the adult female), diameters of some hundreds of microns may be used. If it is desired to limit the diameter of needles for injection syringes for the comfort of the patient, it is good to limit the diameter of the microspheres to 300 microns and more preferably to 100 microns. In contrast, for very short durations of desired effect (for example circadian), the diameter of the microsphere may be reduced to 1 micron.

For most applications in human medicine (duration of action of the active ingredient between a circadian cycle and a menstrual cycle), it is preferable to use microspheres whose diameter is between 5 and 100 microns depending on the active substances.

An essential condition for achieving the dosage form according to the present invention is to have batches of calibrated microspheres, that is to say homogeneous in diameter. If necessary, a separation of the microspheres according to their diameter may be carried out during the manufacture using known processes: for example by cyclonic separators, by sieving using air suction or by sieving in a liquid medium. In practice, it is sufficient if more than 70% of the microspheres have diameters of between 70% and 130% of a specified diameter. If necessary, the ideal dissolution curve, determined by the proposed application, may be approached by mixing batches with different suitable diameters.

Processes for preparing a solid product in the form of microspheres by mechanical abrasion are known in the state of the art. Other processes use for example the suspension of the product in the melted state in the form of microdrops, with stirring, in a liquid vector with which the said product is non-miscible, followed by solidification of the said product. The patent WO 90/13285 describes a process for the manufacture of porous microspheres obtained by spraying, freezing and freeze-drying in a cold gas substances dissolved in a suitable solvent. In order to obtain solid and non-porous microspheres according to the present invention, it has been preferred to develop, for substances which may be maintained in a chemically stable state above the melting point, a process which consists in spraying under pressure and/or by means of hot gas the substance (optionally with additives) in the melted state and rapidly freezing the cloud thus formed in a cold gas.

Furthermore, the particles which are not in compliance with the specifications may be recycled.

Taking into consideration the conditions of use, from a pharmacological point of view, the formulations according to the present invention are particularly suited to substances whose melting temperature is greater than 60° C. and which are thermostable above their melting point (or which may be made thermostable by means of additives) in order to be able to undergo the manufacturing process. An additive may also be used in order to eliminate a phase transition, from a solid phase to another solid phase, which is likely to weaken the structure of the sphere. The process is also suited to mixtures of active substances in solid solution one inside the other.

The present invention will be better understood by means of the figures and examples below. However it is not limited to these embodiments, but only by the content of the claims.

BRIEF DESCRIPTION OF THE FIGURES

FIGS. 10 and 11 show the comparative dissolution profiles of progesterone microspheres and crystals (50 to 100 μm).

FIGS. 14, 15 and 16 show the plasma levels (rabbits) obtained with progesterone by injection of an oil solution of crystals of mean size 44 μm and of microspheres of mean size 44 μm respectively.

In the FIGS. 6–13, and 20–22, the time scales are given in hours; in the FIGS. 14–19, the time scales are given in days, after injection.

EXAMPLE 1

Manufacture of Progesterone Microspheres

Figure 1:
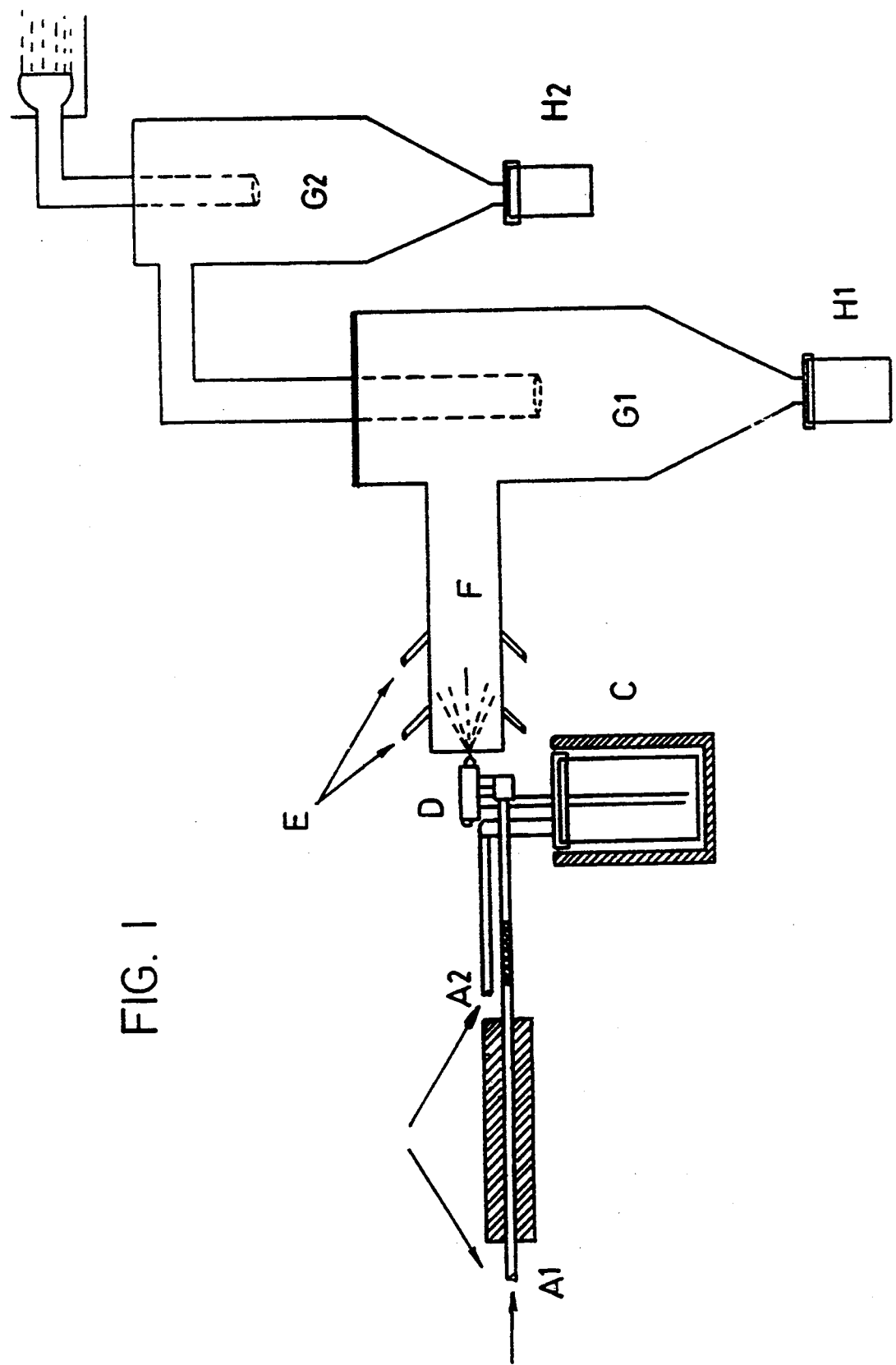
FIG. 1 shows the schematic of the manufacture of microspheres according to the present invention.
Figure 2:
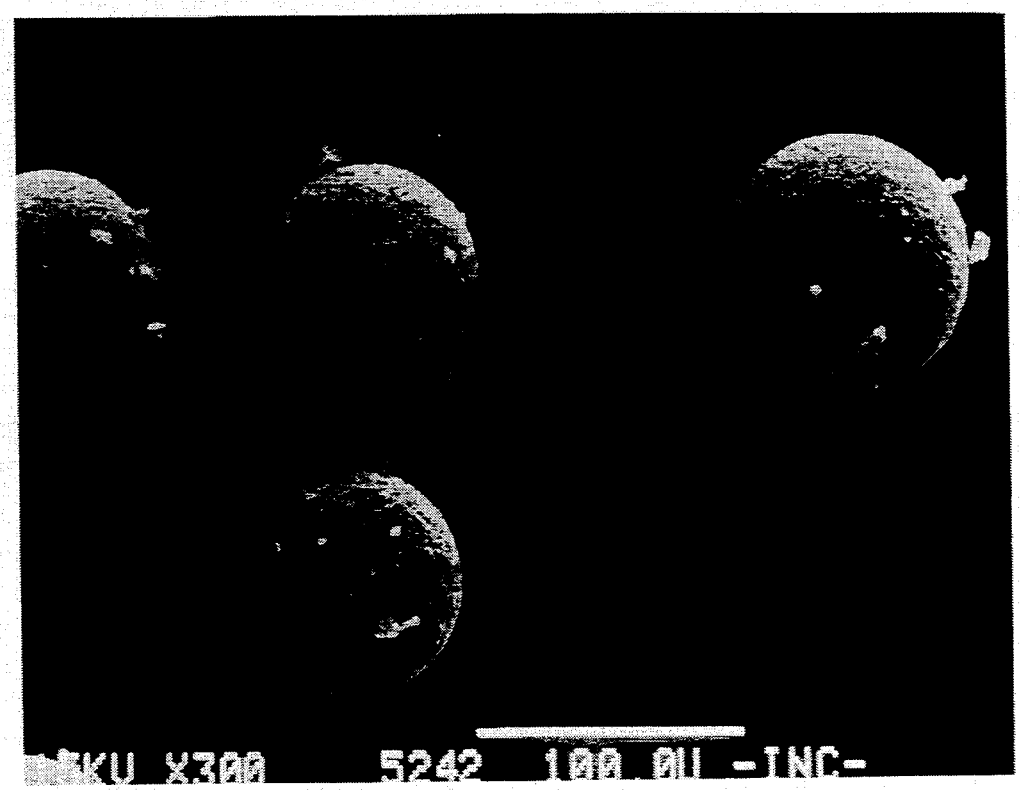
FIG. 2 shows progesterone microspheres (mean diameter=50 μm–100 μm).

We refer to FIG. 1. Preheated nitrogen under pressure is fed by the inlet tube A ↓ 1 ↑ into the spray device and crosses a thermoregulated heating zone B where it is brought to a temperature of between 125° and 130° C. before being admitted into the sprayer D. The sprayer D is connected by a pipe to a heated chamber C in which the progesterone is maintained in the melted state (T=130° C.) and under nitrogen pressure (inlet $A_2$). It is carried by the nitrogen current and mixed with the latter in order to be sprayed into a cloud by the outlet nozzle of the sprayer D and penetrates into the spraying-freezing chamber F. A reservoir E contains liquid nitrogen which evaporates and penetrates by several tubings in the form of ultra-cold gas, at high speed, into the spraying-freezing chamber F where it meets the progesterone cloud. Immediately after their formation by the sprayer, the droplets are surrounded by a current of ice-cold gas which crystallises them into microspheres and prevents them from touching the side walls before their complete solidification. The temperature at the outlet of the spraying-freezing chamber is between −15° C. and −50° C. All the microspheres produced by means of this chamber F have a perfect spherical shape. At the outlet of the chamber F are two cyclonic separators $G_1$ and $G_2$ (of known construction moreover) mounted in series. O. The microspheres are recovered in collecting vessels $H_1$ and $H_2$; at the outlet of the cyclones, the gases pass through a decontaminating filter I in which a slight vacuum relative to the existing pressure prevailing in the first cyclone is maintained by means of a pump. FIG. 2 shows a microphotograph of a fraction (diameter=50 μm to 100 μm) of recovered progesterone microspheres (in an electron microscope).

The IR spectra of the raw material (crystals) and of the microspheres obtained have the same peaks, the UV spectra are similar and the thermograms are practically identical (mp of crystals=130° C., mp of microspheres=129°); no structural degradation of the progesterone therefore occurred during the process.

EXAMPLE 2

The same operating conditions (except that mp=185° C.) are applied to the manufacture of 17-β-estradiol microspheres with the same results.

Figure 3:
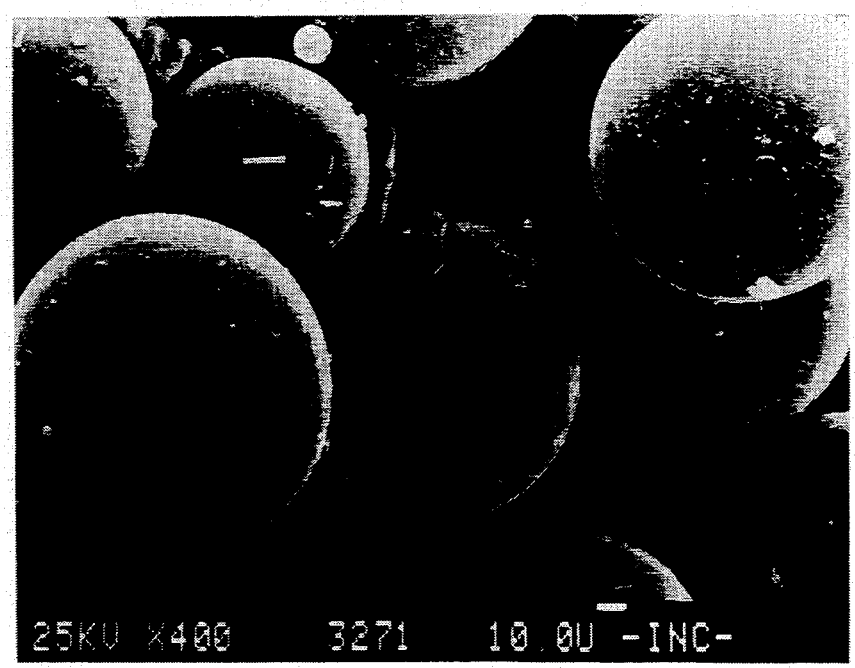
FIG. 3 shows 17-β-estradiol microspheres (mean diameter =100 μm).

FIG. 3 shows a microphotograph of a fraction of these microspheres, of mean diameter 100 μm.

EXAMPLE 3

Particle Size Distribution

Figure 4:
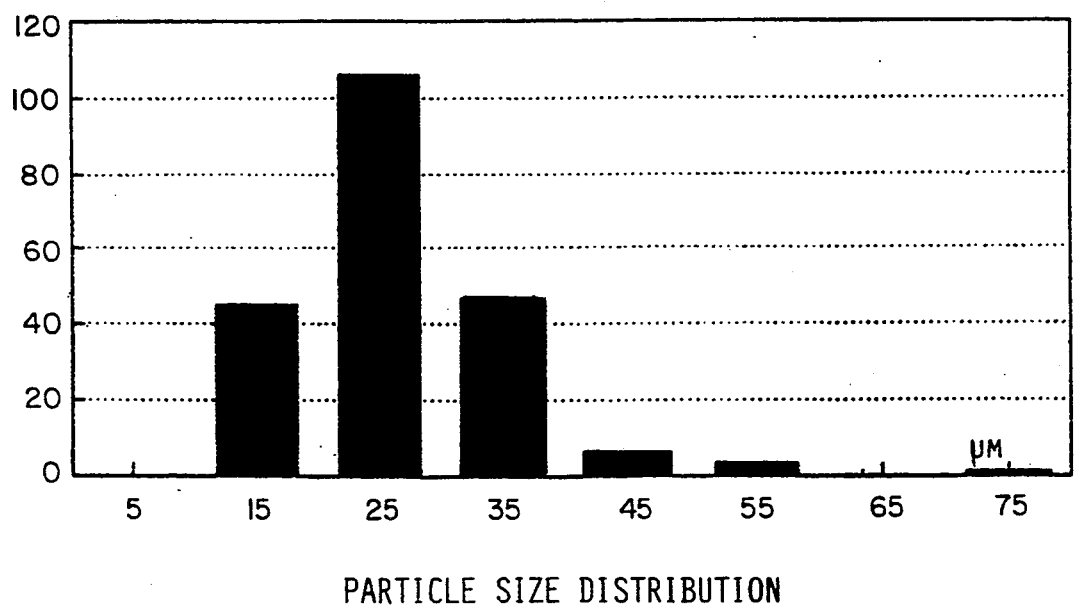
FIG. 4 shows the particle size distribution of a fraction (mean diameter=25 μm) of cholesterol spheres.

Cholesterol microspheres are manufactured by the same operating process as in Example 1. After separation, the fraction of mean diameter 25 μm exhibits the particle size distribution shown in FIG. 4.

EXAMPLE 4

Manufacture of Naproxen Microspheres

The process in Example 1 is used. Operating conditions:

Melting: 160° C. in nitrogen atmosphere.
Sprinkling: by valve with air pressure of 2.0 psi (140 g/cm$^2$)
Freezing: by air at −20° C., under pressure of 4 kg/cm$^2$.
Recovery: by cyclones
Selection: in aqueous medium and by screening according to particle size.

EXAMPLE 5

Progesterone Microspheres

The process in Example 1 is used. Operating conditions:

Melting: 130° C. in nitrogen atmosphere.
Sprinkling: by valve, with air pressure of 0.5 psi (70 g/m$^2$)
Freezing: by air at −20° C., under pressure of 4 kg/cm$^2$.
Recovery: by cyclones
Selection: in aqueous medium and by screening according to particle size.

EXAMPLE 6

17-β-Estradiol

The procedure in Example 1 is used. Operating conditions:

Melting: 180° C. in nitrogen atmosphere.
Sprinkling: by valve, with air pressure of 2.0 psi (140 g/cm$^2$)
Freezing: by air at −10° C., under pressure of 3 kg/cm$^2$
Recovery: by cyclones
Selection: in aqueous medium and by screening according to particle size.

EXAMPLE 7

Indomethazin Microspheres

The procedure in Example 1 is used. Operating conditions:

Melting: 165° C. in nitrogen atmosphere.
Sprinkling: by valve, with air pressure of 1.5 psi (110 g/cm$^2$)
Freezing: by air at −20° C., under pressure of 4 kg/cm$^2$
Recovery: by cyclones
Selection: in aqueous medium and by screening according to particle size.

Comparative UV and IR Spectrophotometric Analysis
Before and After Formation of Microspheres It is necessary to check that no chemical damage of the substances occurs during the spray-freezing process, which could modify their therapeutic properties. The starting materials (crystals) and the microspheres obtained by spray-freezing are compared by UV and IR spectophotometry. UV spectras shall always be superimposable and IR spectras shall correspond. If differences in infrared spectras appear, it shall be checked if they are due to a polymorphism phenomenon, by means of an HPLC setup with diode-array detection. Differential thermal analysis is also used, not only to check the melting points, but also to determine if endothermic or exothermic transitions occur, due either to structure modifications or to a polymorphism, which may influence the microsphere information process, or due to heat-induced chemical reactions.

Equipment used in ultraviolet spectography: Hewlett Packard model 8452A with photodiode arrangement and quartz cell with a beam of 0.1 cm.

Solvents: ethanol for 17-beta-estradiol, progesterone and cholesterol; 0.1N HCl for naproxen, 0.1N sodium hydroxide for indometacin.

The results show no trace of modification.

Equipment used in infrared spectrophotometry: Beckman Acculab 10. Dispersion medium: potassium bromide.

Chromatography: HPLC device with photo diode-array detector, model Waters 990 and Nec powermate 2 workstation.

The results show no modification after the formation of microspheres for indometacin, progesterone, 17-beta-estradiol and naproxen.

Thermal analysis: Shimadzu DSC 50 calorimeter and CR4A workstation.

On the differential thermograms, the measured melting points do not show any chemical degradation of the substances (for example MP crystals = 130° C., MP microspheres = 129° C. for progesterone). The thermograms of progesterone and 17-$\beta$-estradiol show only a morphological modification of the solid crystalline faces.

EXAMPLE 8

Dissolution Curves Progesterone Microspheres

Figure 5:
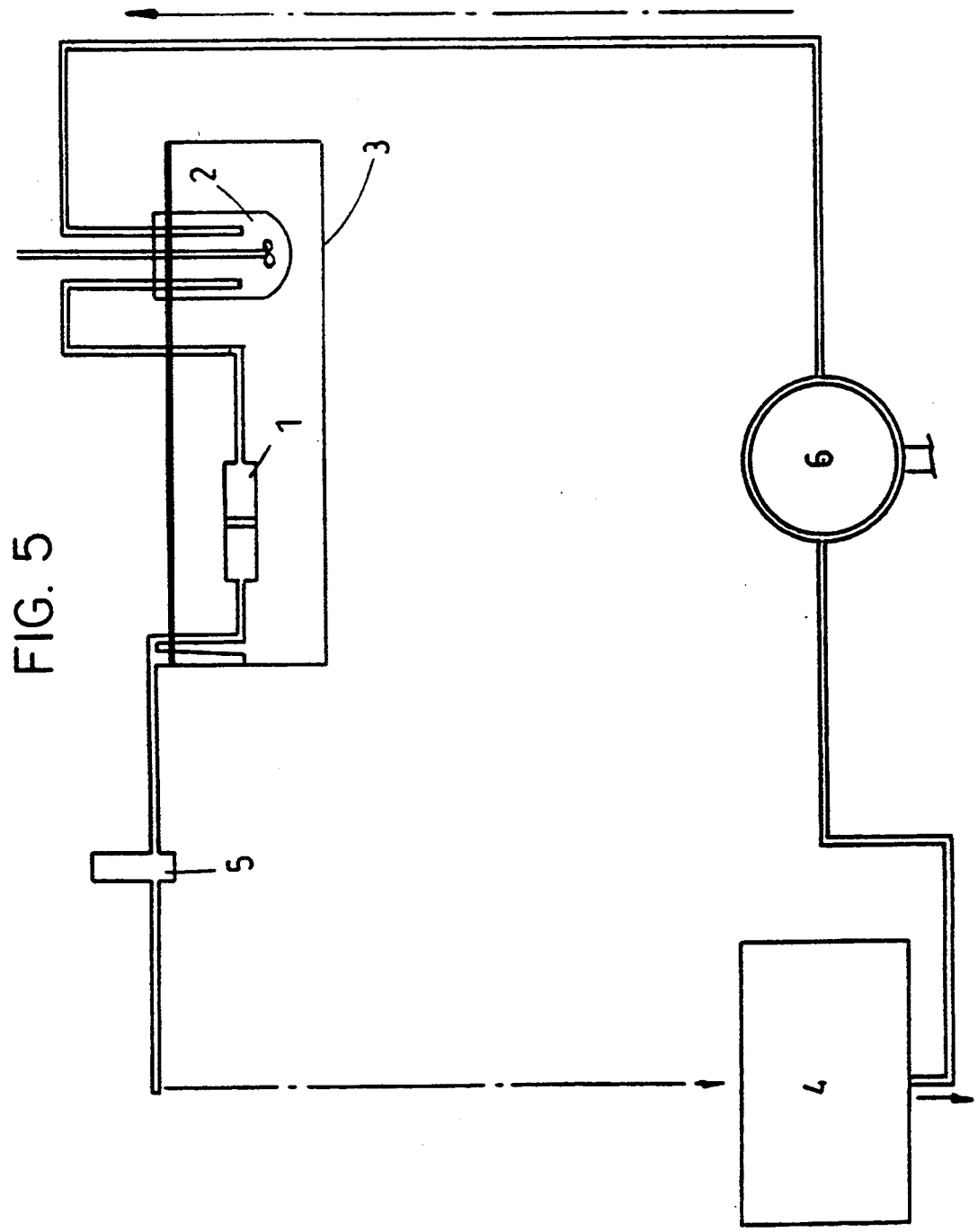
FIG. 5 represents an experimental setup for determining the rate of dissolution of microspheres.

The tests may be carried out either in pure water or in a 1:1 water-polypropylene glycol medium in order to accelerate the dissolution. The experimental setup is shown in FIG. 5. An infusion cell 1, containing the sample, is fed by a reservoir (stirred) of dissolution medium 2; both are kept on a water bath 3. The optical density of the medium at 240 nm is recorded by a spectrophotometer 4 and the medium is returned into the reservoir. A bubble trap 5 and a peristaltic pump 6 complete the circuit.

Figure 6:
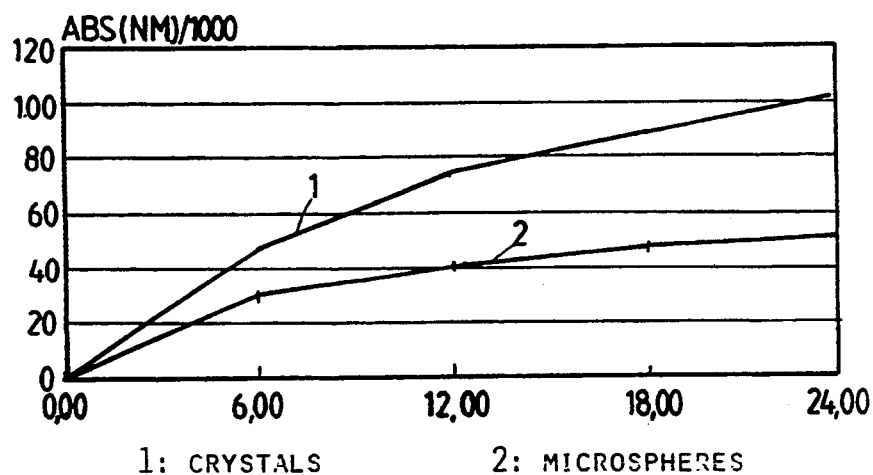
FIG. 6 shows the comparative dissolution profiles of microspheres and progesterone crystals (50–125 μm).
Figure 7:
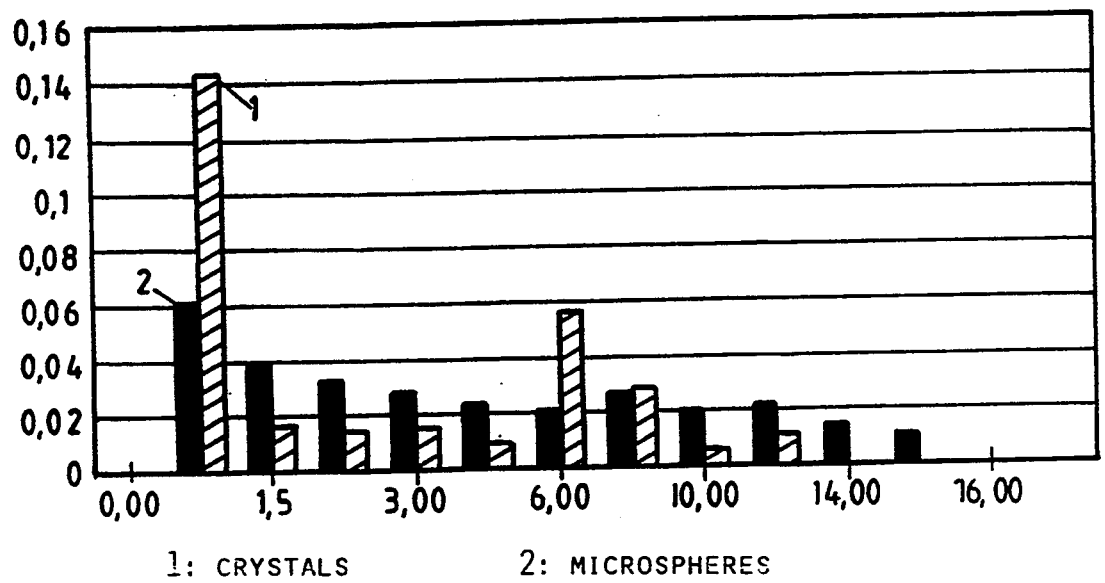
FIG. 7 shows the comparative dissolution rates of progesterone microspheres and crystals (derivatives of optical absorbance versus time).

FIG. 6 shows the dissolution profiles of crystals (curve 1) and microspheres (curve 2) of the same particle size (50–125 μm) measured by the variation of optical absorbance versus time. The test is carried out in a water/PPG 50:50 medium. It appears that the dissolution of microspheres is slower than the dissolution of crystals. FIG. 7 shows the rates of dissolution (derivatives of the variations of optical density versus time) of crystals (1) and microspheres of the same mean particle size (about 150 μm). The particle size distribution of the crystals is more heterogeneous and their dissolution profile is more irregular than that of the microspheres.

EXAMPLE 9

The same test as in Example 8 is carried out with 17-$\beta$-extradiol. The results (not shown) are similar. The following examples show the Comparative reproducibility of the initial parts of the dissolution curves of crystals and microspheres of comparable size, for the same product. The equipment used is the one in FIG. 5. Several (3–6) measurement circuits (dissolution cells and tubings) containing identical samples are processed in parallel by the same peristatic pump and measured simultaneously.

EXAMPLE 10

Dissolution of progesterone crystals: (FIG. 11)/progesterone microspheres (FIG. 10)
Dissolution medium used: $H_2O$ HPLC quality with 0.01% of Tween 80
Sample: 50 mg
Particle size: 50 to 100 microns
Sampling intervals: 0,2,4,8,14,20 hours
Spectrophotometric wavelength: 240 nm

EXAMPLE 11

Dissolution of naproxen microspheres: (FIG. 12)/naproxen crystals (FIG. 13)
The equipment used is that in FIG. 5.
Dissolution medium used: $H_2O$ HPLC quality with 0.01% of Tween 80
Sample: 50 mg
Particle size: 50 to 100 microns
Sampling intervals: 0,1,3,6,9,12,24 hours
Spectrophotometric wavelength: 232 nm

EXAMPLE 12

Figure 8:
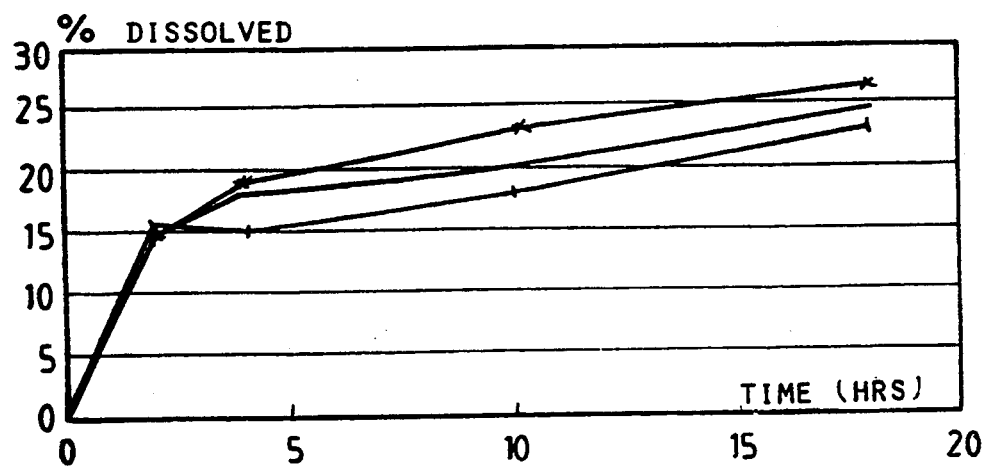
FIGS. 8 and 9 show the comparative dissolution profiles of 17-β-estradiol microspheres and crystals (50 to 100 μm).
Figure 9:
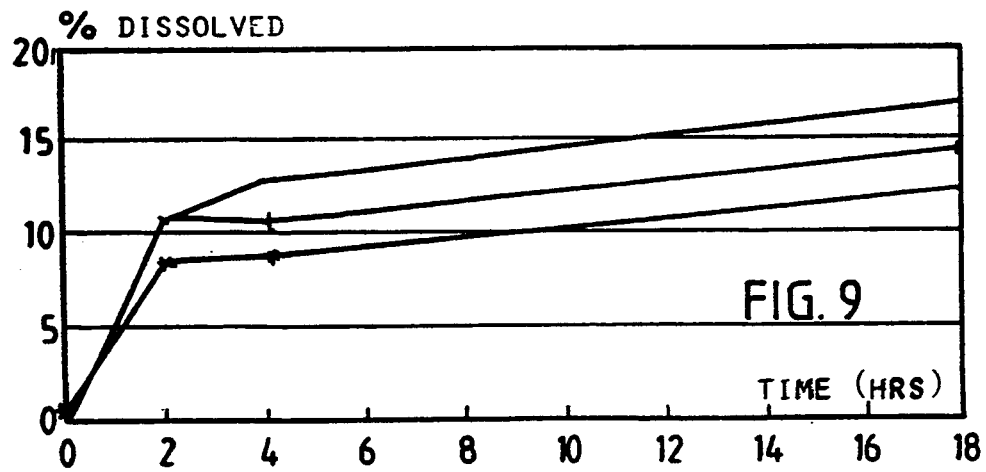
Figure 12:
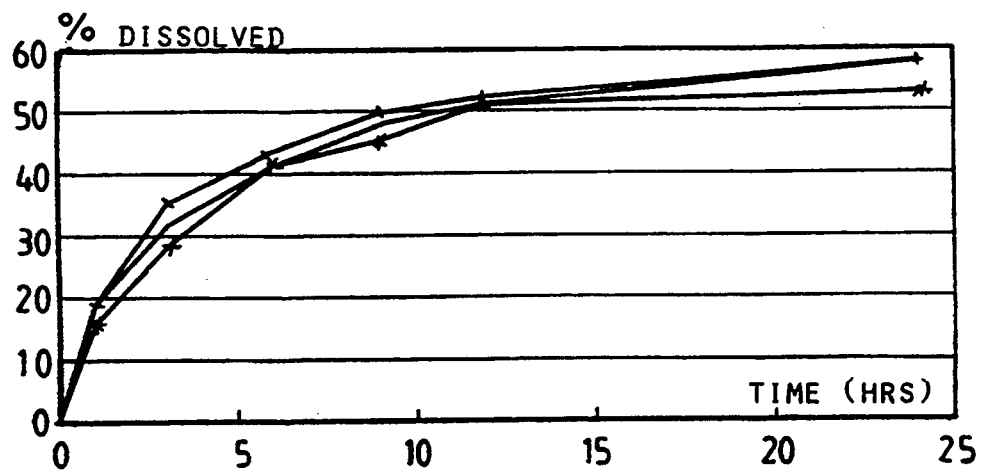
FIGS. 12 and 13 show the comparative dissolution profiles of naproxen microspheres and crystals (50–100 μm).
Figure 13:
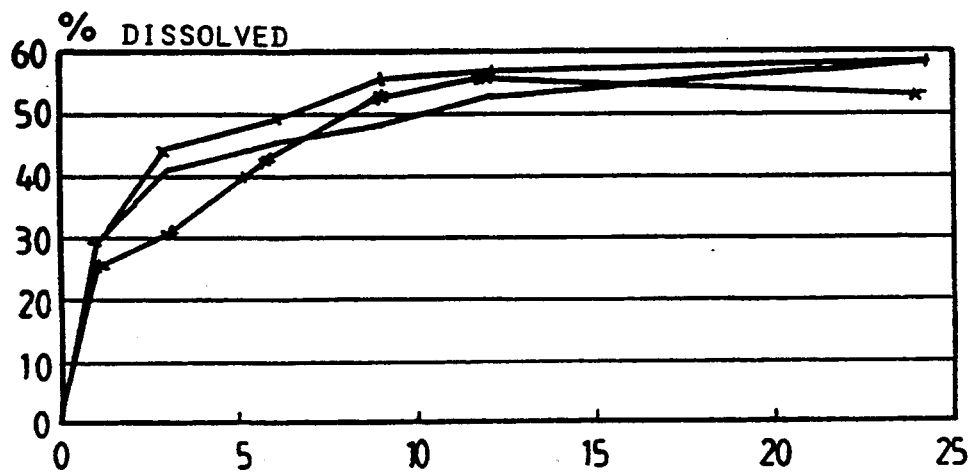

Dissolution of 17-beta-estradiol microspheres: (FIG. 9)/17-beta-estradiol (FIG. 8).
The equipment used is that in FIG. 5
Dissolution medium used: $H_2O$ HPLC quality with 0.01% of Tween 80
Sample: 50 mg
Particle size: 50 to 100 microns
Sampling intervals: 0,2,4,18 hours
Spectrophotometric wavelength: 282 nm All the curves show that the reproducibility of the results and the regularity of the dissolution profiles are better for the microsphere batches than for the crystal batches in the initial part of the dissolution process (which is the most critical moment).

EXAMPLE 13

Injectable Formulations

| Formula No. 1 | |
|---|---|
| Progesterone microspheres | 75 mg |
| Polyethylene glycol 800 | 20 mg |
| Carboxymethylcellulose sodium | 1.66 mg |
| Polysorbate 80 | 2.0 mg |
| Propylparaben | 0.14 mg |
| NaCl | 1.2 mg |
| $H_2O$ cbp | 1 ml |
| Formula No. 2 | |
| 17-beta-estradiol microspheres | 2.5 mg |
| Polyethylene glycol 800 | 20 mg |
| Carboxymethylcellulose sodium | 1.66 mg |
| Polysorbate 80 | 2.0 mg |
| Propylparaben | 0.14 mg |

| -continued | |
|---|---|
| NaCl | 1.2 mg |
| H₂O cbp | 1 ml |
| Formula No. 3 | |
| Naproxen microspheres | 100 mg |
| Carboxymethylcellulose sodium | 5.0 mg |
| Polysorbate 80 | 4.0 mg |
| NaCl | 9.0 mg |
| Benzyl alcohol | 9.0 mg |
| H₂O cbp | 1 ml |

EXAMPLE 14

Figure 16:
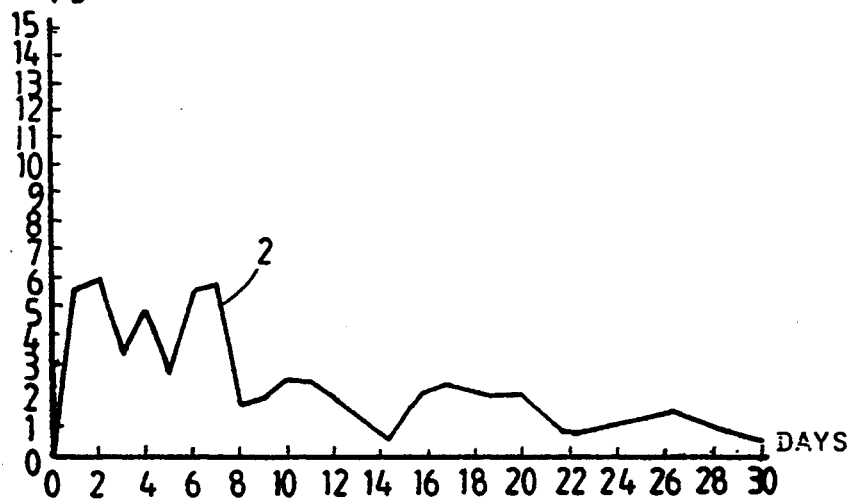

Study of the Plasma Levels of Progesterone in rabbits (FIGS. 14, 15, 16)

The study comprises the comparative evaluation of the effect on the plasma levels in rabbits produced by the parenteral administration of progesterone in the form of an oil solution (0), an aqueous suspension of crystals (1) and an aqueous suspension of microspheres (2) (Formula No. 1, mean particle size: 44 μm).

A single intramuscular dose of progesterone is administered to 10 male rabbits of New Zealand breed of an average weight of 3.5 kg.

The sampling interval is 1,2,4 and 24 hours for 20 days and then every three days up to 30 days.

The 2-ml samples, taken by renopuncture, are centrifuged and kept at −20° C. until their analysis by radioimmunoassay.

EXAMPLE 15

Figure 17:
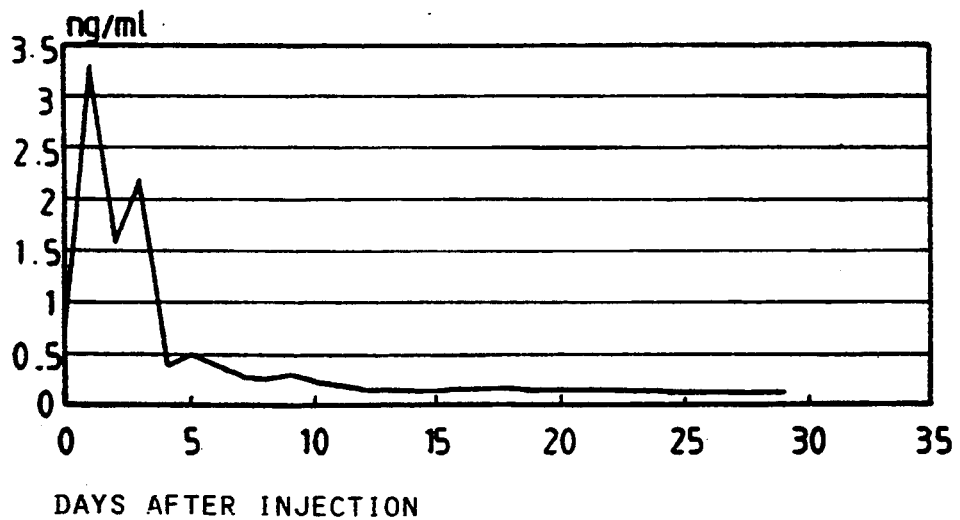
FIGS. 17, 18 and 19 show the plasma levels (rabbits) obtained with 17-β-estradiol by injection of an oil solution of crystals and of microspheres respectively.
Figure 18:
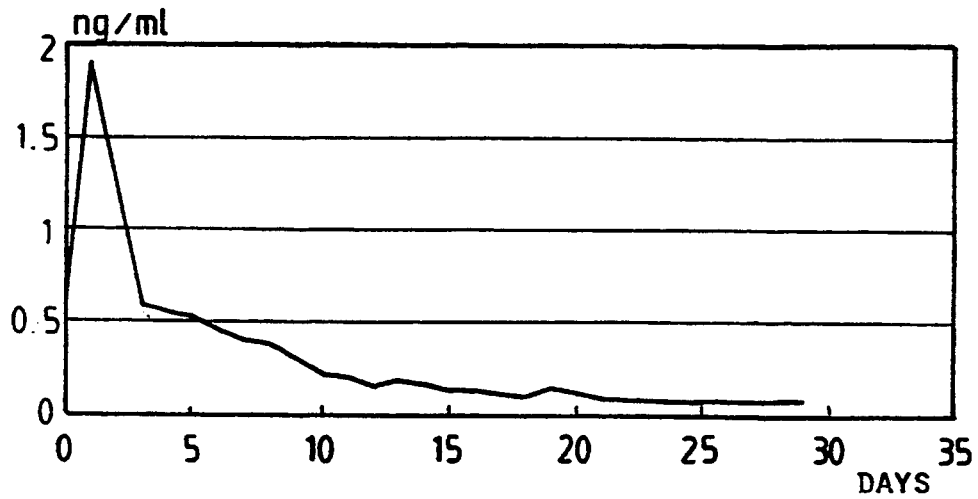
Figure 19:
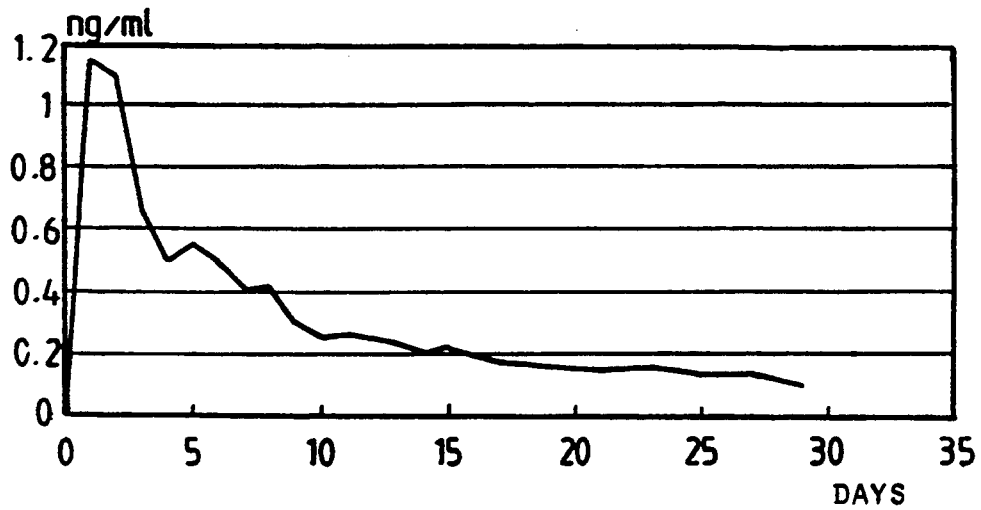

Study of the Plasma Levels of Estradiol in Rabbits (FIGS. 17, 18, 19)

The study comprises the comparative evaluation of the effect on the plasma levels in rabbits produced by the parenteral administration of estradiol in the form of an oil solution (0), an aqueous suspension of crystals (1) and an aqueous suspension of estradiol microspheres (2) (particle size 50–100 μm, Formula no.2).

A single intramuscular dose of 5 mg of estradiol is administered to 8 male rabbits of New Zealand breed of an average weight of 3.5 kg.

The sampling interval is 1,2,4 and 24 hours for 20 days and then every three days up to 30 days.

The 2-ml samples, taken by renopuncture, are centrifuged and kept at −20° C. until their analysis by radioimmunoassay.

EXAMPLE 16

Comparative Evolution of Plasma Levels of Naproxen in Rabbits

Experimental animals: rabbits of New Zealand breed aged about 5 months and weighing on average 3.7 kg.

The reference sample is 5 ml of blood taken by cardiac puncture, followed by the intramuscular administration of 2 ml of the test formula (No 3) into the lower right leg.

The analytical samples were taken at intervals of 30 min for 2 hours and at intervals of 60 min up to the end of 6 hours. In some cases, depending on the kinetic characteristics of the medicinal product, additional samples were taken.

2-ml analytical samples, also taken by cardiac puncture, were placed in a Vacutainer, heparin added, centrifuged at 3000 rpm for 10 min and the plasma separated and frozen in cryotubes at −20° C. until their analysis.

Figure 20:
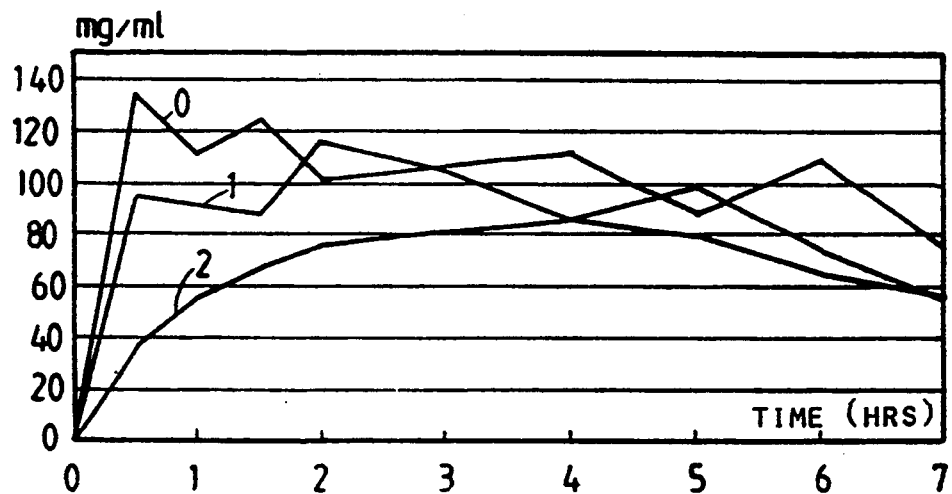
FIG. 20 shows the plasma levels (rabbits) obtained with naproxen by injection of a solution (curve 0) of crystals (curve 1) and of microspheres (curve 2) respectively.
Figure 22:
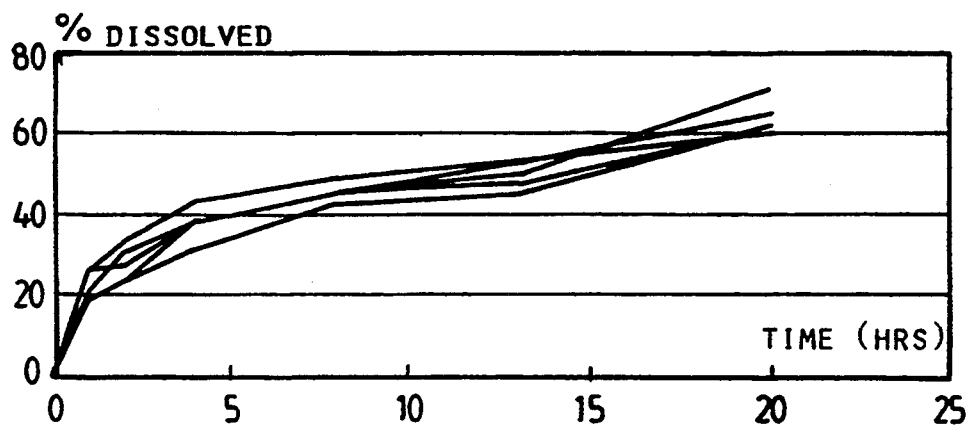
FIGS. 21 and 22 show the comparative dissolution profiles of indomethacin microspheres and crystals (50–100 μm).
Figure 21:
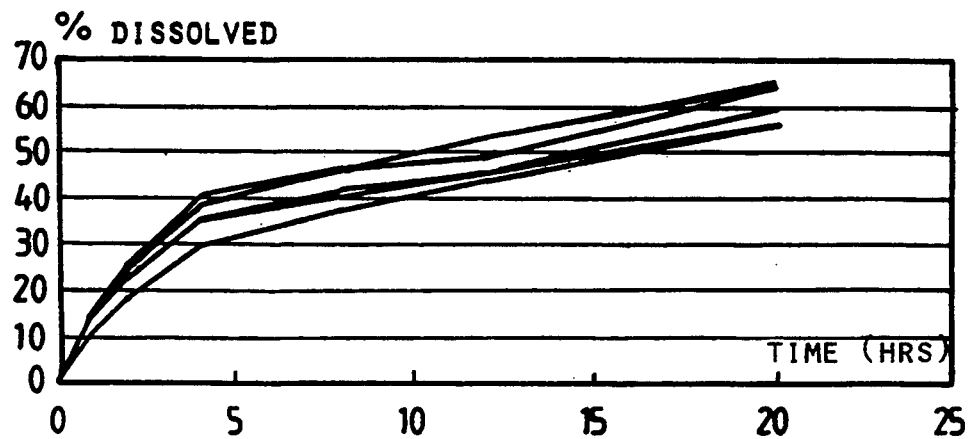

FIG. 20 shows that the variation of the plasmatic levels, obtained after injection of microspheres is much more regular than that obtained after injection of random shave particles (50–100 μm).

In summary, the above disclosed results show that in the initial part of the dissolution process, pharmaceutically active substances exhibit much more reproducible numeric values and much more smoother profiles, in form of batches of calibrated microspheres than in form of random shaped particles. This allows to calculate more accurately a pharmaceutically efficient dose. Moreover, the disappearance of the initial dissolution peak (or at least its dramatic decrease, if compared with crystals or random particles) as well as the delayed and globally extended dissolution process permits to calculate increased unit doses intended to be administered at more spaced periods of time.

Furthermore the above disclosed results show that this type of structure may be used as well for the manufacture of drugs those efficiency-period is relatively short, that is several hours to a few days (for example analgesics), as well as for substances those intended efficiency-period lasts a few weeks. Among the latter, one may cite in particular the use of sexual hormones (as progesterone or 17-β-estradiol) for the manufacture of a contraceptive intended for monthly parenteral injection or for the manufacture of a post-partum contraceptive, or for the manufacture of a medicinal product for parenteral injection intended for the prevention of osteoporosis in menopausal women.

The manufacturing process described above, the spherical structures and the formulations obtained and their use by the parenteral route by injection are naturally not limited to the substances given as examples above, but are applicable to all pharmaceutically active substances, chemically stable during the micronisation, on the condition that the pharmaceutical modifications which permit the microspheres (brief or long duration depending on the diameter, regularisation of the plasma profiles) possess a therapeutic advantage or one of convenience and that the doses to be administered do not exceed a reasonable volume. Depending on the intended application, the method of administration may be chosen from among hypodermic injection, subcutaneous injection, intramuscular injection, intra-articular injection, and intra-rachidian injection.

We claim:

1. Solid, non-porous microspheres of a diameter between 1 and 300 μm, wherein said microspheres consist of an injectable steroid and wherein said microspheres are obtained by spraying said steroid in the melted state to form droplets and rapidly freezing said droplets in a gas.

2. The solid, non-porous microspheres according to claim 1, wherein the diameter of said microspheres is between 5 and 100 μm.

3. The solid, non-porous microspheres according to claim 2, wherein the melting point of said steroid is greater than 60° C. and wherein said steroid is thermostable above the melting point.

4. The solid, non-porous microspheres according to claim 1, wherein said steroid is progesterone.

5. The solid, non-porous microspheres according to claim 1, wherein said steroid is 17-β-estradiol.

* * * * *